United States Patent [19]

Lee et al.

[11] Patent Number: 5,415,619
[45] Date of Patent: May 16, 1995

[54] METHOD OF MANUFACTURING A VASCULAR GRAFT IMPREGNATED WITH POLYSACCHARIDE DERIVATIVES

[75] Inventors: Hai B. Lee; Bung C. Shin; Gilson Khang; Jin H. Lee, all of Taejeon, Rep. of Korea

[73] Assignee: Korea Research Institute of Chemical Tech., Taejeon, Rep. of Korea

[21] Appl. No.: 147,923

[22] Filed: Nov. 5, 1993

Related U.S. Application Data

[63] Continuation of Ser. No. 626,893, Dec. 13, 1990, abandoned.

[30] Foreign Application Priority Data

Dec. 13, 1989 [KR] Rep. of Korea .............. 89-18490

[51] Int. Cl.$^6$ .................. A61F 2/04; A61F 2/06
[52] U.S. Cl. .......................... 600/36; 623/1
[58] Field of Search .............. 623/1, 901, 11; 600/36; 427/2

[56] References Cited

U.S. PATENT DOCUMENTS

| | | | |
|---|---|---|---|
| 4,411,754 | 10/1983 | Kaetsu et al. | 204/159.15 |
| 4,647,505 | 3/1987 | Blackie et al. | 428/396 |
| 4,806,595 | 2/1989 | Noishiki et al. | 525/54.2 |
| 4,836,884 | 6/1989 | McAuslan | 156/629 |
| 4,882,148 | 11/1989 | Pinchuk | 424/423 |
| 4,883,605 | 11/1989 | Putzig | 252/8.551 |
| 4,961,954 | 10/1990 | Goldberg et al. | 427/2 |
| 4,979,959 | 12/1990 | Guire | 523/66 |
| 5,112,873 | 5/1992 | Pike | 521/32 |

FOREIGN PATENT DOCUMENTS

| | | |
|---|---|---|
| 0206025 | 12/1986 | European Pat. Off. . |
| 3097158 | 4/1988 | Japan . |
| 3115554 | 5/1988 | Japan ............ 623/1 |

OTHER PUBLICATIONS

Guidoin, R. et al., *Albumin Coating of a Knitted Polyester Arterial Prosthesis An Alternative to Preclotting*, The annals of Thoracic Surgery, vol. 37, No. 6, (Jun., 1984).

Urry, D. W. et al., *Irradiation crosslinking of the polytetrapeptide of elastin and compounding to dacron to produce a potential prosthetic material with elasticity and strength*, Journal of Biomedical Materials Research, vol. 16, pp. 11-16, (1982).

*Primary Examiner*—David Isabella
*Assistant Examiner*—Debra Brittingham
*Attorney, Agent, or Firm*—Michael L. Dunn

[57] ABSTRACT

A vascular graft fabricated of a polyester fiber, the surface of which is impregnated with biodegradable blood-compatible materials, characterized in that the surface of the said vascular graft comprises carboxylate groups and is impregnated with polysaccharides or their derivatives. The vascular graft is manufactured by treating the hydrophobic surface of a vascular graft fabricated of a polyester fiber to render it more hydrophilic and then impregnating the vascular graft with above polysaccharides or their derivatives by chelate bond with metal ions or physical adsorption in order to increase the adhesion properties and adding glycerin to the impregnated polysaccharides or their derivatives in order to increase the softness so that the impregnated substances may turn into the state of gel by blood at the time of use.

9 Claims, No Drawings

METHOD OF MANUFACTURING A VASCULAR GRAFT IMPREGNATED WITH POLYSACCHARIDE DERIVATIVES

This is a Continuation of application Ser. No. 07/626,893, filed Dec. 13, 1990, abandoned.

TECHNICAL FIELD

The present invention relates to a vascular graft used as an artificial blood vessel and a method for manufacturing the said vascular graft, more particularly to a vascular graft fabricated of a polyester fiber which is impregnated with polysaccharides or their derivatives thereby reducing the porosity of the fabric, preventing blood leakage and making a preclotting process unnecessary.

BACKGROUND OF THE INVENTION

It is very important that materials used for artificial organs in general should not cause any toxic, carcinogenic, pyrogenic or allergic effect nor any adverse tissue or skin reaction, etc. in the body.

In particular, materials of vascular grafts which are used to replace surgically damaged blood vessels should have flexibility as well as anti-thrombogenic properties and be easy to fabricate.

Nylon, polyester, polytetrafluoro ethylene (PTFE), polypropylene, polyacrylonitrile, etc. have been used as materials to fabricate vascular grafts. Among them PTFE and polyester are now widely used since they do not have significant property changes in the body after long term use. Polyester, in particular polyethyleneterephthalate (trade name: Dacron), is most widely used as the material of vascular grafts because it is easy to handle and easy to fabricate.

In case the said polymer materials are used, the fabrication state or porosity of the materials has great significance. The porosity of vascular grafts plays an important role for their long-term patency and overall biological performance. The porosity of the vascular grafts allows easy handling and anastomosis, and good flexibility. It also facilitates transmural ingrowth of connective tissue into the grafts and better healing into the surrounding tissue. Therefore, the porosity is an essential component for long term function of vascular grafts. The main disadvantage of highly porous vascular grafts is their high permeability for blood during implantation. It may result in severe blood leakage through the graft wall. Thus, the grafts must be preclotted with blood before the implantation to obtain zero permeability. Generally the grafts are immersed in or flushed with fresh blood of patient to preclot the wall surface. But the preclotting process is often time-consuming, causes blood transfusion, and may lead to increased usage of the patient's blood. In the case of an emergent patient with large bleeding by an accident, it may be fatal. It is also dangerous when the patient has been systematically heparinized for surgery.

Many research works have been done to develop new vascular grafts, which are blood tight during implantation and thus eliminate the need for preclotting the grafts, and become sufficiently porous to facilitate tissue ingrowth and biological healing. Most commonly used methods include coating or impregnation of the porous graft with a biodegradable component. The coated or impregnated vascular graft is blood tight during the implantation. Due to its gradual degradation and dissolution in the body, the resorbable material creates increasingly large pores in the initially impervious graft, allowing the ingrowth of periprosthetic tissue.

Until now, various proteins have been used as the biodegradable components for coating or impregnation of the grafts. They include albumin, gelatin or elastin, collagen, and fibrin. The vascular grafts pre-treated with these proteins showed little blood loss and faster healing compared to the grafts preclotted with blood.

However, in the case the vascular grafts are impregnated with above proteins, there is a problem that the proteins are easily denatured when the grafts are manufactured. The proteins are also not easy to make compatible with usual storage and sterilization procedures.

Thus, the objective of the present invention is to develop an improved vascular graft fabricated of a polyester fiber which is impregnated with non-proteinaceous materials, polysaccharides or their derivatives, which are biodegradable and biocompatible. The said vascular graft is blood tight during the implantation and persists its high porosity for tissue ingrowth and biological healing.

Consequently, the purpose of the present invention consists in providing an improved artificial blood vessel fabricated of a polyester fiber which is surface-treated and then impregnated with polysaccharides or their derivatives.

SUMMARY OF THE INVENTION

The present invention relates to a vascular graft fabricated of a polyester fiber which is impregnated with biodegradable blood-compatible materials, characterized by the fact that the surface of the said vascular graft is impregnated with polysaccharides or their derivatives with carboxyl groups in their structures.

Besides, the present invention relates to a method for manufacturing a vascular graft by impregnating the surface fabricated of a polyester fiber with biodegradable blood-compatible materials, characterized by the fact that the surface of the said vascular graft is made hydrophilic by chemical or physical treatments and then impregnated with polysaccharides or their derivatives.

DETAILED DESCRIPTION OF THE INVENTION

According to the present invention, the hydrophobic surface of a vascular graft fabricated of a polyester fiber is modified hydrophilic by chemical or physical treatments and then impregnated with polysaccharides or their derivatives as biodegradable blood-compatible materials by chelate bond using metal ions or by physical adsorption.

In the present invention, the surface of the said vascular graft can be changed hydrophilic by a chemical treatment, for example, a treatment with sulfuric acid or perchloric acid, wherein the surface of the fabricated graft is oxidized, or by a physical treatment, wherein the fabric surface of the graft is treated with plasma or corona discharge.

In the said treatment with sulfuric acid, the vascular graft fabricated of polyester is oxidized by being immersed in a solution comprising concentrated sulfuric acid, chromic oxide and distilled water in the volumetric ratio of 10~80%, 10~80% and 20~80%, respectively. By the said treatment, the surface of the polymer fabric gets negative charges by sulfonation reaction and the hydrophilicity of the surface increased.

In the said treatment with perchloric acid, the fabric surface is treated with a solution comprising perchloric acid and saturated solution of potassium perchlorate in the volumetric ratio of 30~90% and 10~70%, respectively, thereby the hydrophilicity getting increased and hydroxyl groups being introduced on the fabric surface.

On the other hand, the said physical treatment with plasma or corona discharge is a method based upon the principle that plasma or corona is discharged from an electrode to activate the surrounding gas layer and the ions or radicals thus activated reacts with the fabric surface, thereby the hydrophilicity getting increase.

The chemically or physically treated surface of the vascular graft has been analyzed by the ESCA (electron spectroscopy for chemical analysis) and the results are shown in the following Table 1.

TABLE 1

Composition of functional groups on the polyester surface.

| Functional group | C—C | C—OH/C—O—C | C=O | COOH/COOC |
|---|---|---|---|---|
| No treatment | 68 | 16 | — | 16 |
| Chemical Treatment | 58.0 | 22.0 | 3.0 | 17 |

As seen from the above Table 1, in case the polyester surface is modified by the treatment according to the present invention, the decrease in C—C bonds and increase in C—OH/C—O—C and C=O bonds, resulting from the oxygens incorporated on the polyester surface, indicate that the hydrophilicity increased.

The vascular graft surface-modified as above is impregnated with biodegradable blood-compatible materials; as biodegradable blood-compatible materials according to the present invention, polysaccharides or their derivatives are used. As polysaccharides or their derivatives used according to the present invention, for example, cellulose, denatured cellulose (C.M.C.), alginic acid or alginates, carboxymethyl alginates (C.M.A.), pectin, carrageenan, chitin or keto acids, xanthane gum, starch or denatured starch, etc. may be used; these materials may be used after undergoing alcoholic purification, etc. or chemical modification.

It is also desirable to use the said polysaccharides after improving their solubility, blood-coagulating property or water-swollen property by modifying their chemical structures so as to let carboxyl groups be introduced in their side chains; the method of letting carboxyl groups be introduced in their chemical structures of the said polysaccharides consists in treating hydroxyl groups in their structures with sodium hydroxide and then adding chloroacetates, thereby obtaining carboxymethylated polysaccharides with the esterification value, which shows the degree of reaction of hydroxyl groups, ranging between 0.64 and 3.

The polysaccharides obtained as above are agitated and purified in 20 80% alcohol solution and then are dried in a desiccator at the temperature under 80° C.

The polysaccharides obtained by purification with alcohol or polysaccharide derivatives modified by carboxylation as described above are used as impregnation materials for the said surface-treated vascular graft.

According to the present invention, the polysaccharides impregnated into the surface-treated vascular grafts are bound onto the surface of the polyester fabric by physical adsorption or by chemical binding, i.e., by chelate formation of metal ions with carboxy functional groups.

The said binding can be schematically shown as follows. In the following examples, "A" means the polyester surface.

EXAMPLE 1

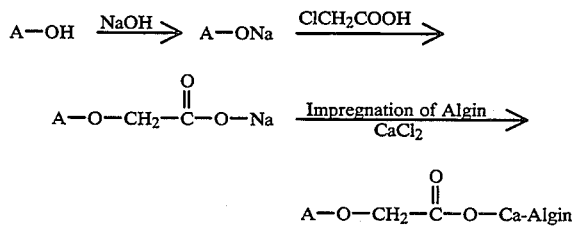

EXAMPLE 2

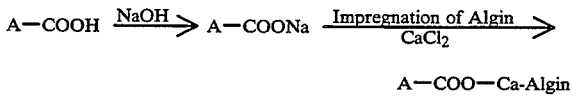

A—COO—Ca-Algin

The surface-treated polyester fabric has lots of hydroxyl groups on its surface as shown in the Table 1 and therefore needs carboxylation for desirable impregnation of polysaccharides. The carboxylation of hydroxyl groups on the polyester fiber surface comprises the process of letting alkalization proceed for about 1 hour at the temperature of 60° C. in 30% sodium hydroxide. By this treatment, hydrogen ions of hydroxyl groups are replaced to sodium ions. The polyester fabric is then reacted with 78% chloroacetic acid for 1 hour at the temperature of about 70° C., and the polyester fabric which is carboxymethylated by replacement reaction of sodium ions and acetic acid is obtained.

The fabric treated as above, which contains functional groups formed by carboxylation reaction of hydroxyl groups in addition to the formerly formed carboxy functional groups, has good affinity with such polysaccharioles as alginic acid and its coherency can be increased by adding such multivalent ions as calcium ion, which lead to binding with the fabric surface.

The following Table 2 shows the test results of water permeability and porosity of the vascular graft into which polysaccharides or their derivatives are chemically or physically combined and impregnated according to the present invention described above.

TABLE 2

| Water permeability and porosity tests of vascular grafts. | | | |
|---|---|---|---|
| Classification | Water permeability (ml/cm2 · min)* | Coating weight (g/g) | porosity (%) |
| KR - plain fabric** | 668 | — | 75 |
| KR - impregnated fabric** | 0 | 0.6 | — |
| Cooly - L.P. (high density) | 54 | — | 60 |
| V.P. 50K - triple fabric | 1100 | — | 74 |

TABLE 2-continued

Water permeability and porosity tests of vascular grafts.

| Classification | Water permeability (ml/cm2 · min)* | Coating weight (g/g) | porosity (%) |
|---|---|---|---|
| V.P. 50K-impregnated fabric | 200 | 0.4 | — |

*measured at 120 mmHg
**KR denotes the product according to the present invention.

The said water permeability and porosity are factors affecting blood leakage occurring when a vascular graft is implanted into the body, and tissue cell ingrowth and endothelial cell proliferation after implantation; if the fabric of polyester fiber is too dense, the problem of blood leakage is solved but the tissue cell ingrowth is hindered; if the fabric is too loose, the reverse problem occurs.

Consequently, in order to solve the problem of blood leakage while using a relatively loose fabric, the preclotting has been so far applied, whereas according to the present invention, the impregnation of biodegradable blood-compatible substances into the fabric can prevent blood leakage at the time of implant operation, and facilitate the growth of tissue cells into the interstices of the fabric as the impregnated substances are slowly decomposed in the body, thereby all the said problems being able to be solved.

As shown in the above given Table 2, the water permeability and porosity of the vascular graft (KR-plain fabric) according to the present invention are much greater than cooly-L.P and less than V.P 50K- triple fabric.

The water permeability of KR-impregnated fabric, which is a vascular graft impregnated with polysaccharides, is remarkably reduced since the impregnated substances come in contact with water and swell, thereby inhibiting water from permeating. In addition, regardless of the coating weight, the impregnated substances come in contact with water and blood and exist in the state of swollen gel, keep very soft and do not influence the intrinsic properties of the vascular graft.

Also, in case a vascular graft is directly implanted without preclotting, blood rapidly coagulates on the surface of the vascular graft and coats the surface, thereby blood leakage being prevented and adhesion of endothelial cells being facilitated by the formed membrane.

The blood coagulation properties of the vascular graft according to the above given Table 2, measured by whole blood clotting test method, are shown in the following Table 3.

TABLE 3

Whole blood clotting time of vascular grafts

| Classification | Whole blood clotting time (minutes) |
|---|---|
| KR-plain fabric* | 8.1 |
| KR-impregnated fabric* | 2.6 |
| Cooly-L.P. (high density) | 6.5 |
| Woven double velour | 6.2 |

*KR denotes the product according to the present invention

As shown in the above given Table 3, the whole blood clotting time of KR-impregnated fabric is 2.6 minutes, which is three to four times as short as that of the conventional polyester graft.

As described above, the vascular graft according to the present invention is different from the conventional vascular graft in that it is manufactured by treating the hydrophobic surface of a graft fabricated of a polyester fiber by chemical or physical methods and thus increasing the hydrophilicity, then impregnating the graft with polysaccharides or their derivatives by chelate bonding with metal ions or physical adsorption in order to increase the adhesion properties, and adding glycerin to the impregnated polysaccharides or their derivatives in order to increase the softness so that the impregnated substances may turn into the state of gel by blood at the time of use.

Consequently, the said vascular graft does not need washing with saline solution before being used in operations, is easy to handle, and its surface keeps very soft. Furthermore, since the bond between the fabric and the polysaccharides is relatively strong, there is no possibility of the impregnated substances being detached by the blood stream in the body. In addition, the initial blood clotting proceeds faster than in vascular grafts which is impregnated with protein. It is an advantage, too, that the water permeability is very low due to the impregnated substances.

The present invention is demonstrated in detail by the following examples.

EXAMPLE 1

A vascular graft, fabricated of a polyester fiber, of the conventional crimped tube type, is put in a 0.25 torr vacuum reactor, in which plasma is generated with a power supply of 50 mA and 200 volts at 100 KHz while oxygen is being purged at the rate of 80 ml/min, thereby oxidizing the surface of the said vascular graft.

Subsequently, the surface-oxidized graft is taken out, immersed in a 1.5% aqueous solution of alginates and air bubbles are completely eliminated.

The vascular graft which is free of air bubbles and impregnated with alginates is taken out, immersed in a 1% calcium chloride solution for 5 minutes, immersed in 80% and 95% ethanol and is dried in a 60° C. vacuum desiccator.

The dried vascular graft is immersed in a 4% E.D.-T.A salt for 30 minutes, washed with 20% and 80% ethanol in succession and dried. The vascular graft thus manufactured is sterilized with ethylene oxide (E.O.) gas or Γ-ray (2.5 Mrad) and used as an artificial blood vessel.

EXAMPLE 2

The inside of a vascular graft, fabricated of polyester, is treated with corona with a power supply of 150 mA, 200 Volt at 100 KHz thereby oxidizing the surface of the graft. The surface-oxidized vascular graft is put in a 30% sodium hydroxide solution for 30 minutes at the temperature of 60° C., thereby alkalizing its surface and repeatedly washed with distilled water until the pH becomes 7 to 8.

Subsequently, the vascular graft treated as above is put in 2 to 5% carboxymethyl alginates and air bubbles are eliminated in a vacuum oven. When air bubbles are completely removed, the graft is taken out, put in a 2% calcium chloride solution for 5 minutes at the room temperature, so that a binding reaction proceeds between the carboxy functional groups formed on the surface of the graft and the alginates. The graft is then dehydrated with 80% and 95% ethanol and dried, put in a 10% sodium acetate solution and the pH adjusted to 5.5 by adding an acetic acid and agitated for 30 minutes.

The vascular graft treated as above is taken out, dehydrated in 20% and 80% ethanol and dried in a vacuum desiccator. The vascular graft thus manufactured is sterilized with E.O gas or Γ-ray and used as an artificial blood vessel.

EXAMPLE 3

A vascular graft, fabricated of polyester, is put in a solution containing concentrated sulfuric acid, chromic oxide and distilled water at the ratio of 30%, 30% and 40% in the mentioned order for 10 minutes at the temperature of 60° C., thereby oxidizing the surface of the vascular graft.

The vascular graft treated as above is put in a 40% sodium hydroxide solution for 30 minutes at the temperature of 50° C., thereby alkalizing its surface, and washed several times with distilled water so that the remaining residues after reaction are removed.

Subsequently, the vascular graft treated as above is immersed in a 4% carboxymethyl alginate solution and air bubbles are eliminated in a vacuum oven. The graft is then put in a 2% calcium chloride solution for 5 minutes, dehydrated with ethanol and dried, and by the same processes as in Example 2 the impregnated artificial blood vessel is manufactured.

EXAMPLE 4

A vascular graft, fabricated of polyester, is put in a mixture solution of 70% perchloric acid and saturated potassium perchlorate solution at the ratio of 3 to 2 for 10 minutes at the temperature of 60° C., taken out and washed with distilled water, put in a 40% sodium hydroxide solution for 20 minutes at the temperature of 60° C. to alkalize its surface. The graft is then put in a 80% chloroacetic acid solution for 1 hour at the temperature of 70° C. so that carboxymethyl groups may bind to the alkalized surface.

After the said reaction, sodium carbonate is added in the said solution, so that the pH of the solution may be adjusted to the range of 7 to 8 and the vascular graft is washed with distilled water until the remaining residues are removed. The vascular graft the surface of which is carboxymethylated as above is immersed in a 1.5% alginate solution, degassed in a vacuum oven, put in a 2% calcium chloride solution for 5 minutes, and by the same processes as in the Example 2, the impregnated artificial blood vessel is manufactured.

What is claimed is:

1. A method for manufacturing a vascular graft by impregnating biodegradable blood-compatible materials into a porous tube fabricated of a polyester fiber, which comprises the steps of:
   (1) treating said porous tube to render said porous tube hydrophilic;
   (2) impregnating said porous hydrophilic tube with a polysaccharide or polysaccharide derivative; and
   (3) coating an inner and an outer surface of said impregnated tube with a polysaccharide or polysaccharide derivative to obtain said vascular graft,
   steps (1), (2), and (3) occurring sequentially.

2. The method as defined in claim 1, wherein said porous tube is rendered hydrophilic by chemical treatment.

3. The method of claim 2, wherein the porous tube is rendered hydrophilic by treatment with a solution of sulfuric acid and chromic oxide.

4. The method as defined in claim 3, wherein the treatment with a solution of sulfuric acid and chromic oxide consists of immersing the porous tube in a solution comprising concentrated sulfuric acid, chromic oxide and distilled water in the volumetric ratio of 10 to 80%, 10 to 80% and 20 to 80%, respectively, to render the porous tube hydrophilic.

5. The method of claim 2, wherein the porous tube is rendered hydrophilic by hyperoxidation treatment.

6. The method as defined in claim 1, wherein the polysaccharides or their derivatives are impregnated into the porous hydrophilic tube and cross-linked by chelate binding with metal ions.

7. The method as defined in claim 6, wherein the said polysaccharides or their derivatives are bound by cross-linking onto the inner and outer surfaces of the impregnated tube.

8. The method as defined in claim 2, wherein the polysaccharides or their derivatives are impregnated into the porous hydrophilic tube and cross-linked by chelate binding with metal ions.

9. The method as defined in claim 1, wherein the said polysaccharides or their derivatives are bound by cross-linking onto the inner and outer surfaces of the impregnated tube.

* * * * *